United States Patent
Yamaguchi

(10) Patent No.: US 12,097,802 B2
(45) Date of Patent: Sep. 24, 2024

(54) SAFE DRIVING DETERMINATION APPARATUS

(71) Applicant: ISUZU MOTORS LIMITED, Tokyo (JP)

(72) Inventor: Kazuhiko Yamaguchi, Fujisawa (JP)

(73) Assignee: ISUZU MOTORS LIMITED, Tokyo (JP)

( * ) Notice: Subject to any disclaimer, the term of this patent is extended or adjusted under 35 U.S.C. 154(b) by 0 days.

(21) Appl. No.: 17/908,906

(22) PCT Filed: Mar. 9, 2021

(86) PCT No.: PCT/JP2021/009365
§ 371 (c)(1),
(2) Date: Sep. 1, 2022

(87) PCT Pub. No.: WO2021/182481
PCT Pub. Date: Sep. 16, 2021

(65) Prior Publication Data
US 2024/0198903 A1  Jun. 20, 2024

(30) Foreign Application Priority Data
Mar. 11, 2020 (JP) .................. 2020-042079

(51) Int. Cl.
*B60Q 9/00* (2006.01)
*B60K 28/02* (2006.01)
*G06V 20/59* (2022.01)

(52) U.S. Cl.
CPC ............ *B60Q 9/00* (2013.01); *B60K 28/02* (2013.01); *G06V 20/597* (2022.01)

(58) Field of Classification Search
CPC ......... B60Q 9/00; G06V 20/597; B60K 28/02
See application file for complete search history.

(56) References Cited

U.S. PATENT DOCUMENTS

| 7,675,296 B2 * | 3/2010 | Lambert ............... G01B 7/003 340/576 |
| 2010/0007480 A1 | 1/2010 | Uozumi et al. |

(Continued)

FOREIGN PATENT DOCUMENTS

| CN | 109758167 A | 5/2019 |
| CN | 109774469 A | 5/2019 |

(Continued)

*Primary Examiner* — John A Tweel, Jr.
(74) *Attorney, Agent, or Firm* — PROCOPIO, CORY, HARGREAVES & SAVITCH LLP

(57) ABSTRACT

A safe driving determination apparatus includes an angle value identification part that identifies an angle value indicating a face direction angle of a driver with respect to the traveling direction of a vehicle, an offset value determination part that determines an offset value of the angle value corresponding to an imaging direction of the imaging device with respect to a face of the driver using the angle value identified by the angle value identification part over a predetermined period of time, and a determination part that starts determining whether or not the driver is in a state of being inattentive to the road ahead on the basis of a relationship between the offset value and the angle value after the offset value determination part determines the offset value.

5 Claims, 4 Drawing Sheets

(56) References Cited

U.S. PATENT DOCUMENTS

| | | | |
|---|---|---|---|
| 2013/0151030 A1* | 6/2013 | Tatsumi | G06V 20/597 |
| | | | 701/1 |
| 2019/0013529 A1 | 1/2019 | Moon et al. | |
| 2019/0143993 A1 | 5/2019 | Aoi et al. | |
| 2019/0144003 A1 | 5/2019 | Hyuga et al. | |

FOREIGN PATENT DOCUMENTS

| CN | 109795409 A | 5/2019 |
|---|---|---|
| JP | 2008-097445 A | 4/2008 |
| JP | 2016-207174 A | 12/2016 |
| JP | 2019-070875 A | 5/2019 |
| JP | 2019-070876 A | 5/2019 |
| KR | 10-2011-0062651 A | 6/2011 |
| WO | 2020-031873 A1 | 2/2020 |

\* cited by examiner

SAFE DRIVING DETERMINATION APPARATUS

CROSS-REFERENCE TO RELATED APPLICATIONS

The present application is a U.S. National Stage entry of PCT Application number PCT/JP2021/009365, filed on Mar. 9, 2021, which claims priority under 35 U.S.C § 119(a) to Japanese Patent Application No. 2020-042079, filed on Mar. 11, 2020, contents of which are incorporated herein by reference in their entirety.

TECHNICAL FIELD

The present disclosure relates to a safe driving determination apparatus.

BACKGROUND ART

Conventionally, an apparatus has been proposed that determines whether a driver is inattentive to the road ahead (looking aside) according to a face direction of a driver while driving a vehicle, and alerts the driver if the driver is determined to be inattentive to the road ahead. This apparatus issues an alarm if a driver's face direction angle deviates from a reference direction, which is the average face direction when a driver is not looking aside, for more than a predetermined period of time (for example, see Patent Document 1).

PRIOR ART

Patent Document

Patent Document 1: Japanese Unexamined Patent Application Publication No. 2019-70875

SUMMARY OF INVENTION

Problems to be Solved by the Invention

However, since it takes time to determine the reference direction, an initial value such as a traveling direction of the vehicle is used as the reference direction in a period before the reference direction is determined. If a determination is made on the basis of the initial value in this manner, the apparatus may erroneously issue the alarm even though the driver is not looking aside, in a case where the difference between the reference direction and the initial value is large.

The present disclosure focuses on this point, and an object thereof is to prevent or reduce the issuance of an alarm even though the driver is not looking aside.

Means for Solving the Problems

A safe driving determination apparatus according to an embodiment of the present disclosure is a safe driving determination apparatus for acquiring an angle value indicating a face direction angle of a driver by using a traveling direction of a vehicle as a reference after capturing an image of the driver of the vehicle with an imaging device to determine whether or not the driver is in a state of being inattentive to the road ahead on the basis of the acquired angle value, the apparatus including an angle value identification part that identifies an angle value indicating a face direction angle of at least one of i) a face direction angle of the driver in a yaw direction with respect to the traveling direction or ii) a face direction angle of the driver in a pitch direction with respect to the traveling direction, an offset value determination part that determines an offset value of the angle value corresponding to an imaging direction of the imaging device with respect to a face of the driver using the angle value identified by the angle value identification part over a predetermined period of time, and a determination part that starts determining whether or not the driver is in a state of being inattentive to the road ahead on the basis of a relationship between the offset value and the angle value after the offset value determination part determines the offset value.

The offset value determination part may determine a new offset value if a percentage of a period during which a face direction of the driver is within a predetermined range is greater than a threshold value, within a predetermined offset value calculation period.

The offset value determination part does not have to determine the new offset value while the determination part determines that the driver is in a state of being inattentive to the road ahead.

If the determination part determines that the driver is not in a state of being inattentive to the road ahead, the determination part may switch an operation between continuing or stopping making the determination on the basis of whether or not the offset value determination part has updated the offset value.

If the offset value determination part has not updated the offset value, the determination part may stop determining whether or not the driver is in a state of being inattentive to the road ahead.

The safe driving determination apparatus further includes a warning part that issues a warning to the driver if it is determined that the driver of the vehicle is in a state of being inattentive to the road ahead, wherein the warning part may issue the warning to the driver on condition that the offset value determination part determines the offset value.

Effect of the Invention

According to the present disclosure, it is possible to prevent or reduce the issuance of an alarm even though the driver is not looking aside.

DESCRIPTION OF EMBODIMENTS

<Configuration of Vehicle S>

Figure 1:
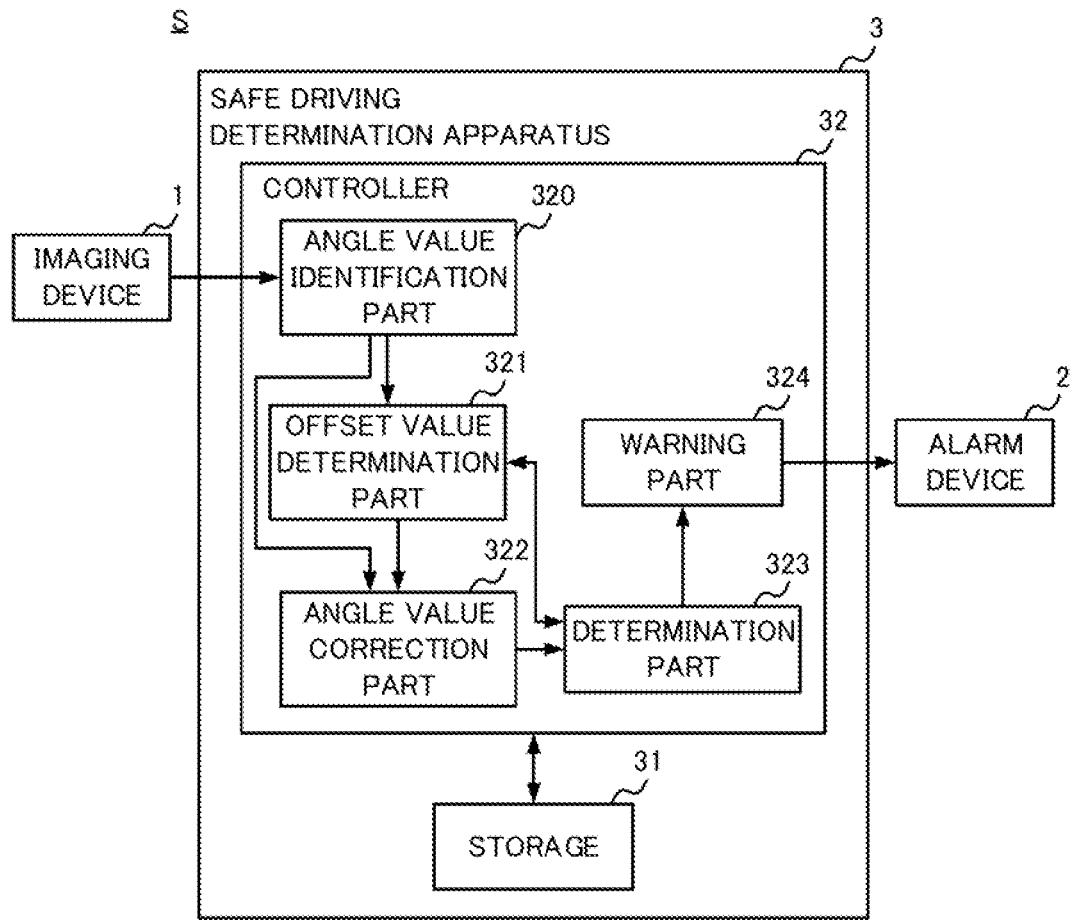
FIG. 1 shows a configuration of a vehicle S according to the present disclosure.

FIG. 1 shows a configuration of a vehicle S according to the present disclosure. The vehicle S includes an imaging device 1, an alarm device 2, and a safe driving determination apparatus 3.

The imaging device 1 is provided to a driver's seat of the vehicle S, and includes a CCD camera, for example. The imaging device 1 captures an image of a driver sitting in the driver's seat from the front to generate a captured image. For example, the imaging device 1 captures an image of a driver's face while the vehicle S is traveling, and generates the captured image that enables identification of the driver's face direction angle with respect to the traveling direction of the vehicle S. The imaging device 1 outputs the generated captured image to the safe driving determination apparatus 3.

Figure 2A:
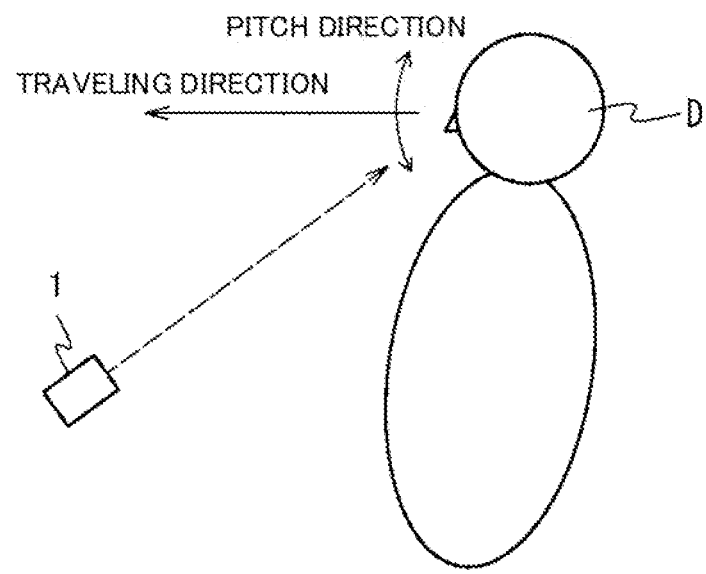
FIG. 2A shows a relationship between an imaging device 1 and a driver's face direction angle.
Figure 2B:
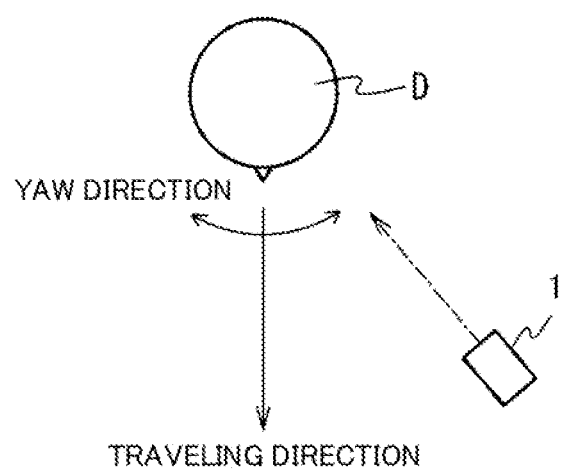
FIG. 2B shows a relationship between an imaging device 1 and a driver's face direction angle.

FIGS. 2A and 2B shows a relationship between the imaging device 1 and the driver's face direction angle. FIG. 2A shows a side view of a driver D, and FIG. 2B shows a top view of the driver D. As shown in FIGS. 2A and 2B, the imaging device 1 is not in front of a driver D's face, but is provided diagonally downward from the driver D's face, for example.

The alarm device 2 is a device that issues a warning to the driver on the basis of notification from the safe driving determination apparatus 3 that the driver is inattentive to the road ahead (for example, looking aside) while driving. The alarm device 2 includes a speaker for issuing an alarm, a display part for displaying a warning screen, and a vibration generation part for generating vibration, for example. It should be noted that the alarm device 2 may issue the warning by combining at least two of sound, display, and vibration.

The safe driving determination apparatus 3 includes a storage 31 and a controller 32. The safe driving determination apparatus 3 captures the image of the driver of the vehicle S with the imaging device 1 to identify an angle value indicating the driver's face direction angle when referenced to the traveling direction of the vehicle. The safe driving determination apparatus 3 determines whether or not the driver is in a state of being inattentive to the road ahead, on the basis of the identified angle value. If the safe driving determination apparatus 3 determines that the driver is in the state of being inattentive to the road ahead, the safe driving determination apparatus 3 notifies the alarm device 2 to issue the warning.

The storage 31 includes a storage medium such as a Read Only Memory (ROM), a Random Access Memory (RAM), and a hard disk. The storage 31 stores a program executed by the controller 32, which will be described later. The storage 31 stores information on the driver's face direction angle, for example.

The control unit 32 is a Central Processing Unit (CPU), for example. The controller 32 functions as an angle value identification part 320, an offset value determination part 321, an angle value correction part 322, a determination part 323, and a warning part 324 by executing the program stored in the storage 31. The controller 32 identifies the driver's face direction angle, and stores the driver's face direction angle in the storage 31.

The angle value identification part 320 identifies the angle value indicating at least one of i) a yaw angle value indicating the driver's face direction angle in the yaw direction relative to the traveling direction of the vehicle S (FIG. 2B) or ii) a pitch angle value indicating the driver's face direction angle in the pitch direction relative to the traveling direction of the vehicle S (FIG. 2A).

The angle value identification part 320 identifies the angle value on the basis of the captured image captured by the imaging device 1. The angle value identification part 320 continuously identifies the angle value at a predetermined interval (for example, 100 second interval). The angle value identification part 320 notifies the offset value determination part 321 and the angle value correction part 322 about the identified angle value.

The offset value determination part 321 uses the angle values identified by the angle value identification part 320 over a predetermined time period (for example, 100 seconds) to determine an offset value for the angle value corresponding to the imaging direction of the imaging device 1 relative to the driver's face. The offset value is a value for correcting the angle value, identified by the angle value identification part 320 with respect to the imaging direction of the imaging device 1, to the angle value with respect to the reference direction, which is the average direction of the face when the driver is not looking aside.

The offset value determination part 321 determines a statistical value such as the mean or median of the angle values identified by the angle value identification part 320 over the predetermined period of time as the offset value, for example. The offset value determination part 321 determines at least one of i) a yaw offset value indicating the offset value of the yaw angle value or ii) a pitch offset value indicating the offset value of the pitch angle value, as an offset value.

The offset value determination part 321 determines a new offset value if the percentage of the period during which the driver's face direction is within a predetermined range is greater than a threshold value (for example, 70 seconds), within a predetermined offset value calculation period (for example, 100 seconds). Here, the period during which the driver's face direction is within the predetermined range is a period of time when the yaw angle value of the driver's face is within 30 degrees from the front direction of the vehicle to the left or right, for example.

The offset value determination part 321 may determine a new offset value if the percentage of the period during which at least one of the driver's face direction angle, a driver's head position, or a speed of the vehicle S is within a predetermined range is greater than a threshold value, for example. The offset value determination part 321 notifies the angle value correction part 322 about the determined offset value.

It should be noted that if the offset value determination part 321 determines the offset value while the determination part 323 determines that the driver is in the state of being inattentive to the road ahead, the face direction of the driver in a state of looking aside is set to the reference direction. Therefore, the offset value determination part 321 does not determine a new offset value while the determination part 323 determines that the driver is in the state of being inattentive to the road ahead.

Specifically, the offset value determination part 321 acquires, from the determination part 323, a determination as to whether or not the driver is in the state of being inattentive to the road ahead. The offset value determination part 321 notifies the angle value correction part 322 about the offset value determined at a previous time without updating the offset value if the determination acquired from the determination part 323 indicates that the driver is in the state of being inattentive to the road ahead. On the other hand, if the determination acquired from the determination part 323 indicates that the driver is not in the state of being inattentive to the road ahead, the newly determined offset value is notified to the angle value correction part 322. The offset value determination part 321 notifies the determination part 323 whether or not the offset value notified to the angle value correction part 322 is a newly determined offset value.

Thus, the offset value determination part 321 switches whether or not to update the offset value on the basis of the determination as to whether or not the driver is in the state of being inattentive to the road ahead acquired from the determination part 323, thereby preventing the notification of the erroneous offset value to the angle value correction part 322.

The angle value correction part 322 corrects the angle value identified by the angle value identification part 320 on the basis of the offset value determined by the offset value determination part 321. For example, the angle value correction part 322 corrects the yaw angle value on the basis of the yaw offset value, and corrects the pitch angle value on the basis of the pitch offset value. The angle value correction part 322 notifies at least one of the corrected yaw angle value or pitch angle value to the determination part 323 as the corrected angle value.

After the offset value determination part 321 determines the offset value, the determination part 323 starts determining whether or not the driver is in the state of being inattentive to the road ahead, on the basis of the relationship between the offset value and the angle value identified by the angle value identification part 320. The determination part 323 acquires the angle value corrected on the basis of i) the offset value determined by the offset value determination part 321 and ii) the angle value identified by the angle value identification part 320, from the angle value correction part 322. The determination part 323 acquires from the offset value determination part 321 whether or not the offset value determination part 321 has updated the offset value. The determination part 323 notifies the warning part 324 about the determination as to whether or not the driver is in the state of being inattentive to the road ahead.

If the determination part 323 determines that the driver is in the state of being inattentive to the road ahead, said determination part 323 notifies the offset value determination part 321 that the driver is in the state of being inattentive to the road ahead. On the other hand, if the determination part 323 determines that the driver is not in the state of being inattentive to the road ahead, the determination part 323 switches an operation between continuing or stopping the determination, on the basis of whether or not the offset value determination part 321 has updated the offset value.

Specifically, if the offset value determination part 321 has updated the offset value while the determination part 323 determines that the driver is not in the state of being inattentive to the road ahead, the determination part 323 determines whether or not the driver is in the state of being inattentive to the road ahead on the basis of said offset value. On the other hand, if the offset value determination part 321 has not updated the offset value, the determination part 323 stops determining whether or not the driver is in the state of being inattentive to the road ahead. By having the determination part 323 operate in this manner, the determination part 323 can be restricted from erroneously determining that the driver is in the state of being inattentive to the road ahead since the offset value determination part 321 does not update the offset value. As a result, the determination part 323 can restrict the warning part 324 from erroneously notifying the driver that he/she is in the state of being inattentive to the road ahead when the driver is not in the state of being inattentive to the road ahead.

If the determination part 323 determines that the driver of the vehicle S is in the state of being inattentive to the road ahead, the warning part 324 issues the warning to the driver. More specifically, the warning part 324 is notified from the determination part 323 to issue the warning to the driver on condition that the determination part 323 determines that the driver is in the state of being inattentive to the road ahead and that the offset value determination part 321 has updated the offset value. The warning part 324 may be notified by the offset value determination part 321 that the offset value has been updated. When the warning part 324 is notified by the determination part 323 to issue the warning, the warning part 324 notifies the alarm device 2 to issue the warning.

<Offset Value Determination Process>

Figure 3:
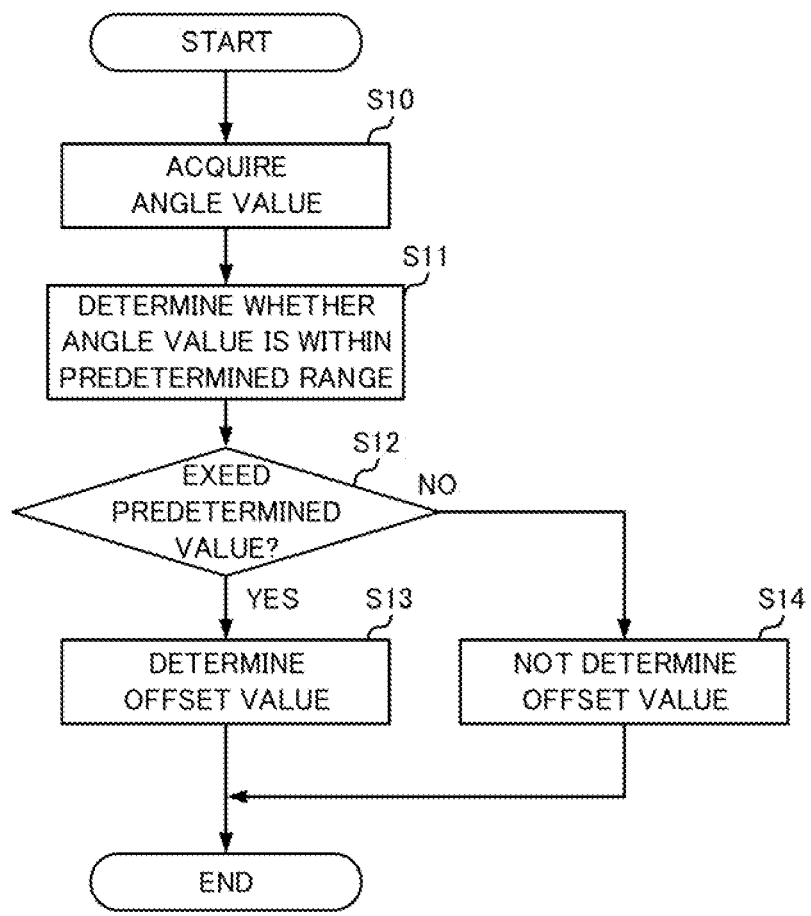
FIG. 3 is a flowchart of a process of an offset value determination part 321 determining an offset value.

FIG. 3 is a flowchart of a process of the offset value determination part 321 determining the offset value. The offset value determination part 321 acquires the angle value identified by the angle value identification part 320 during the immediately previous offset value calculation period (step S10). The offset value determination part 321 determines whether or not each of the acquired angle values is within the predetermined range (step S11).

Subsequently, the offset value determination part 321 determines whether or not the percentage of angle values within the predetermined range among the acquired angle values is greater than a threshold value (step S12). If the percentage of angle values within the predetermined range among the angle values identified during the offset value calculation period is greater than the threshold value (YES in step S12), the offset value determination part 321 determines the offset value from each of said angle values (step S13).

On the other hand, if the percentage of angle values within the predetermined range is less than the threshold value (NO in step S12), the offset value determination part 321 does not determine the offset value (step S14). The offset value determination part 321 repeats the process from S10 to S14 every predetermined time (for example, 1 second). By having the offset value determination part 321 operate in this manner, it is possible to restrict the angle value correction part 322 from correcting the angle value to an erroneous angle value and the determination part 323 from making an erroneous determination on the basis of the erroneous angle value.

<Operation of Determining Offset Value and Determining State of being Inattentive to the Road Ahead>

Figure 4:
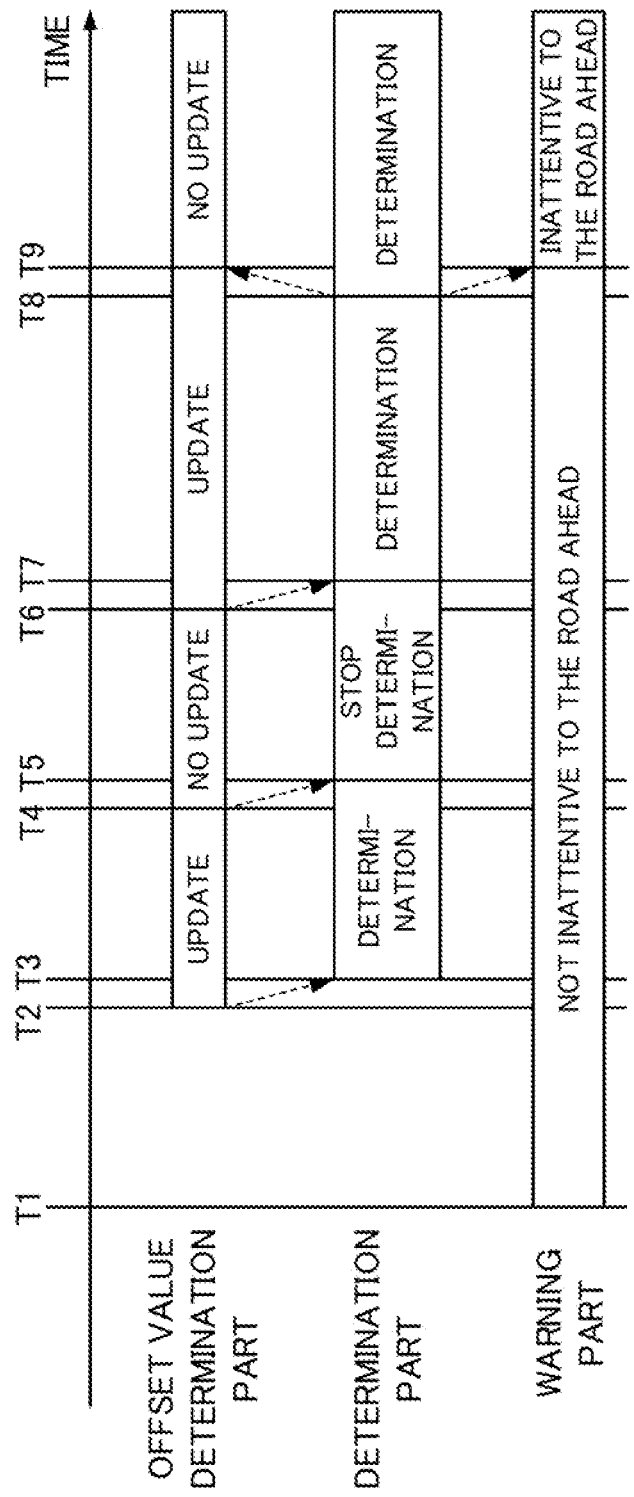
FIG. 4 shows an operation of the offset value determination part 321, a determination part 323, and a warning part 324.

FIG. 4 shows an operation of the offset value determination part 321, the determination part 323, and the warning part 324. The vertical axis in FIG. 4 shows i) an operating status of the offset value determination part 321 in the upper row, ii) an operating status of the determination part 323 in the middle row, and iii) an operating status of the warning part 324 in the lower row. The horizontal axis in FIG. 4 shows time.

At a time T1 (for example, when the engine of the vehicle S is started), the offset value determination part 321 starts identifying the driver's face direction in order to calculate the offset value. From the time T1 to a time T2, the offset value determination part 321 acquires the angle value identified by the angle value identification part 320. The length from the time T1 to the time T2 corresponds to the offset value calculation period. At the time T2, the offset value determination part 321 determines the offset value.

At the time T2, the offset value determination part 321 determines the offset value on the condition that the percentage of angle values within the predetermined range among the angle values identified by the angle value identification part 320 over the offset value calculation period is greater than the threshold value.

At a time T3, which is after the offset value determination part 321 determines the offset value at the time T2, the determination part 323 starts determining whether or not the driver is in the state of being inattentive to the road ahead on the basis of the angle value corrected by the angle value correction part 322 using the offset value.

In this way, the determination part 323 starts determining whether or not the driver is in the state of being inattentive to the road ahead at the time T3, which is a time later than the time T2 at which the offset value determination part 321 first determines the offset value after starting up the vehicle S. This allows the determination part 323 to make a determination on the basis of the angle value corrected by using the offset value based on the driver, thereby preventing from erroneously determine on whether or not the driver is in the state of being inattentive to the road ahead.

The offset value determination part 321 stops updating the offset value at a time T4 if the percentage of angle values within the predetermined range among the angle values identified by the angle value identification part 320 during the offset value calculation period is less than the threshold value.

If the offset value determination part 321 stops updating the offset value at the time T4, the determination part 323 stops determining whether or not the driver is in the state of being inattentive to the road ahead at a time T5. As described above, the determination part 323 stops making the determination, such that the determination part 323 does not determine that "the driver is in the state of being inattentive to the road ahead" if the percentage of angle values within the predetermined range becomes less than the threshold value because the driver changing his/her posture, for example. This prevents the warning part 324 from erroneously issuing the warning for inattentiveness.

At a time T6, the offset value determination part 321 resumes updating the offset value on the basis of the fact that the percentage of angle values within the predetermined range among the angle values identified by the angle value identification part 320 during the predetermined time is greater than the threshold value. If the offset value determination part 321 resumes updating the offset value at the time T6, the determination part 323 resumes determining whether or not the driver is in the state of being inattentive to the road ahead at a time T7.

Thus, the determination part 323 determines whether or not the driver is in the state of being inattentive to the road ahead at the time T7 on the basis of the updated offset value at the time T6, such that the determination part 323 can determine whether or not the driver is in the state of being inattentive to the road ahead even when the driver continues driving without looking aside after checking a mirror, for example.

If the determination part 323 determines that "the driver is in the state of being inattentive to the road ahead" at a time T8, the determination part 323 notifies the offset value determination part 321 and the warning part 324 that "the driver is in the state of being inattentive to the road ahead." At a time T9, the offset value determination part 321 stops determining the offset value on the basis of the notification from the determination part 323 indicating that "the driver is in the state of being inattentive to the road ahead." At the time T9, the warning part 324 notifies the alarm device 2 to issue the warning.

Thus, at the time T9, the offset value determination part 321 stops updating the offset value, such that the determination part 323 continues making a determination on the basis of the angle value corrected by using the offset value at the time T9. This prevents the offset value determination part 321 from determining an erroneous offset value due to, for example, the driver continuing to look aside, and so the determination part 323 can be restricted from making the erroneous determination.

<Effect of Safe Driving Determination Apparatus 3>

As described above, the controller 32 includes the angle value identification part 320 that identifies the angle value, which is the driver's face direction angle, and the offset value determination part 321 that determines the offset value of the angle value. After the offset value determination part 321 determines the offset value, the determination part 323 starts determining whether or not the driver is in the state of being inattentive to the road ahead.

Therefore, in the vehicle S, the angle value can be corrected by using the offset value based on the driver's face direction angle, thus preventing from erroneously determine on whether or not the driver is in the state of being inattentive to the road ahead. This allows the determination part 323 to prevent or reduce the issuance of the alarm even though the driver is not looking aside, on the basis of the erroneous determination.

The present disclosure is explained on the basis of the exemplary embodiments. The technical scope of the present disclosure is not limited to the scope explained in the above embodiments and it is possible to make various changes and modifications within the scope of the disclosure. For example, all or part the apparatus can be configured with any unit which is functionally or physically dispersed or integrated. Further, new exemplary embodiments generated by arbitrary combinations of them are included in the exemplary embodiments of the present disclosure. Further, effects of the new exemplary embodiments brought by the combinations also have the effects of the original exemplary embodiments.

DESCRIPTION OF SYMBOLS 1 imaging device
2 alarm device
3 safe driving determination apparatus
31 storage
32 controller
320 angle value identification part
321 offset value determination part
322 angle value correction part
323 determination part
324 warning part

The invention claimed is:
1. A safe driving determination apparatus for acquiring an angle value indicating a face direction angle of a driver by using a traveling direction of a vehicle as a reference after capturing an image of the driver of the vehicle with an imaging device to determine whether or not the driver is in a state of being inattentive to a road ahead on a basis of the acquired angle value, the apparatus comprising:
an angle value identification part that identifies an angle value indicating a face direction angle of at least one of i) a face direction angle of the driver in a yaw direction with respect to the traveling direction or ii) a face direction angle of the driver in a pitch direction with respect to the traveling direction;
an offset value determination part that determines an offset value of the angle value corresponding to an imaging direction of the imaging device with respect to a face of the driver using the angle value identified by the angle value identification part over a predetermined period of time; and a determination part that starts determining whether or not the driver is in a state of being inattentive to the road ahead on the basis of a relationship between the offset value and the angle value after the offset value determination part determines the offset value, wherein the offset value determination part determines a new offset value if a percentage of a period during which a face direction of the driver is within a predetermined range is greater than a threshold value, within a predetermined offset value calculation period.

2. The safe driving determination apparatus according to claim 1, wherein the offset value determination part does not determine the new offset value while the determination part determines that the driver is in a state of being inattentive to the road ahead.

3. The safe driving determination apparatus according to claim 1, wherein if the determination part determines that the driver is not in a state of being inattentive to the road ahead, the determination part switches an operation between continuing or stopping making the determination on the basis of whether or not the offset value determination part has updated the offset value.

4. The safe driving determination apparatus according to claim 3, wherein if the offset value determination part has not updated the offset value, the determination part stops determining whether or not the driver is in a state of being inattentive to the road ahead.

5. The safe driving determination apparatus according to claim 1, further comprising:

a warning part that issues a warning to the driver if it is determined that the driver of the vehicle is in a state of being inattentive to the road ahead, wherein the warning part issues the warning to the driver on condition that the offset value determination part determines the offset value.

* * * * *